(12) United States Patent
Hoffmann

(10) Patent No.: US 6,553,990 B2
(45) Date of Patent: Apr. 29, 2003

(54) PROCESS FOR CHANGING THE CONCENTRATION IN AN ANESTHESIA APPARATUS

(75) Inventor: Karsten Hoffmann, Griebel/Kasseedorf (DE)

(73) Assignee: Dräger Medizintechnik GmbH (DE)

( * ) Notice: Subject to any disclaimer, the term of this patent is extended or adjusted under 35 U.S.C. 154(b) by 24 days.

(21) Appl. No.: 09/867,289

(22) Filed: May 29, 2001

(65) Prior Publication Data
US 2002/0023643 A1 Feb. 28, 2002

(30) Foreign Application Priority Data
Aug. 22, 2000 (DE) .......................... 100 41 005

(51) Int. Cl.$^7$ ............................................ A61M 16/10
(52) U.S. Cl. ........................ 128/203.12; 128/203.25; 128/204.21
(58) Field of Search ...................... 128/203.12, 203.14, 128/203.25, 204.18, 204.21, 204.26, 205.24, 207.14, 207.18

(56) References Cited

U.S. PATENT DOCUMENTS

| | | | | |
|---|---|---|---|---|
| 4,702,242 A | * | 10/1987 | Broddner et al. ...... | 128/205.13 |
| 5,094,235 A | * | 3/1992 | Westenskow et al. .. | 128/203.12 |
| 5,237,987 A | * | 8/1993 | Anderson et al. ...... | 128/204.18 |
| 5,322,057 A | * | 6/1994 | Raabe et al. .......... | 128/200.16 |
| 5,509,406 A | * | 4/1996 | Kock et al. ............ | 128/200.24 |
| 5,520,169 A | * | 5/1996 | Georgieff et al. ...... | 128/203.29 |
| 5,615,669 A | * | 4/1997 | Olsson et al. .......... | 128/203.12 |
| 5,727,545 A | * | 3/1998 | Psaros .................... | 128/203.12 |
| 5,730,119 A | * | 3/1998 | Lekholm ................ | 128/200.24 |
| 5,918,597 A | * | 7/1999 | Jones et al. ............ | 128/204.23 |
| 5,931,160 A | * | 8/1999 | Gilmore et al. ........ | 128/204.18 |
| 6,152,131 A | * | 11/2000 | Heinonen .............. | 128/204.18 |
| 6,422,237 B1 | * | 7/2002 | Engel et al. ........... | 128/204.18 |

FOREIGN PATENT DOCUMENTS

DE 40 04 034 C2 11/1990

* cited by examiner

Primary Examiner—William C. Doerrler
Assistant Examiner—Mohammad M. Ali
(74) Attorney, Agent, or Firm—McGlew and Tuttle, P.C.

(57) ABSTRACT

A process, system and apparatus for changing the concentration in an anesthesia apparatus with a fresh gas metering unit (14) and a pressure sensor (17) in the breathing circuit, with a volume displacement device (1) in the inspiration branch and a PEEP/$P_{MAX}$ valve (7) in the expiration branch. The fresh gas metering unit (14), the pressure sensor (17), the volume displacement unit (1) and the PEEP/$P_{MAX}$ valve (7) are connected to an evaluating and control unit (15). To bring about a rapid change in the concentration of the anesthetic or fresh gas supplied in the breathing circuit without additional design effort on the anesthesia apparatus the volume displacement device (1) is rinsed, either under the control of the fresh gas supply or under the control of the speed at which the volume displacement device (1) is returned. The rinsing takes place simultaneously with the regular respiration operation of the anesthesia apparatus, which may take place in a volume-controlled or pressure-controlled manner.

13 Claims, 1 Drawing Sheet

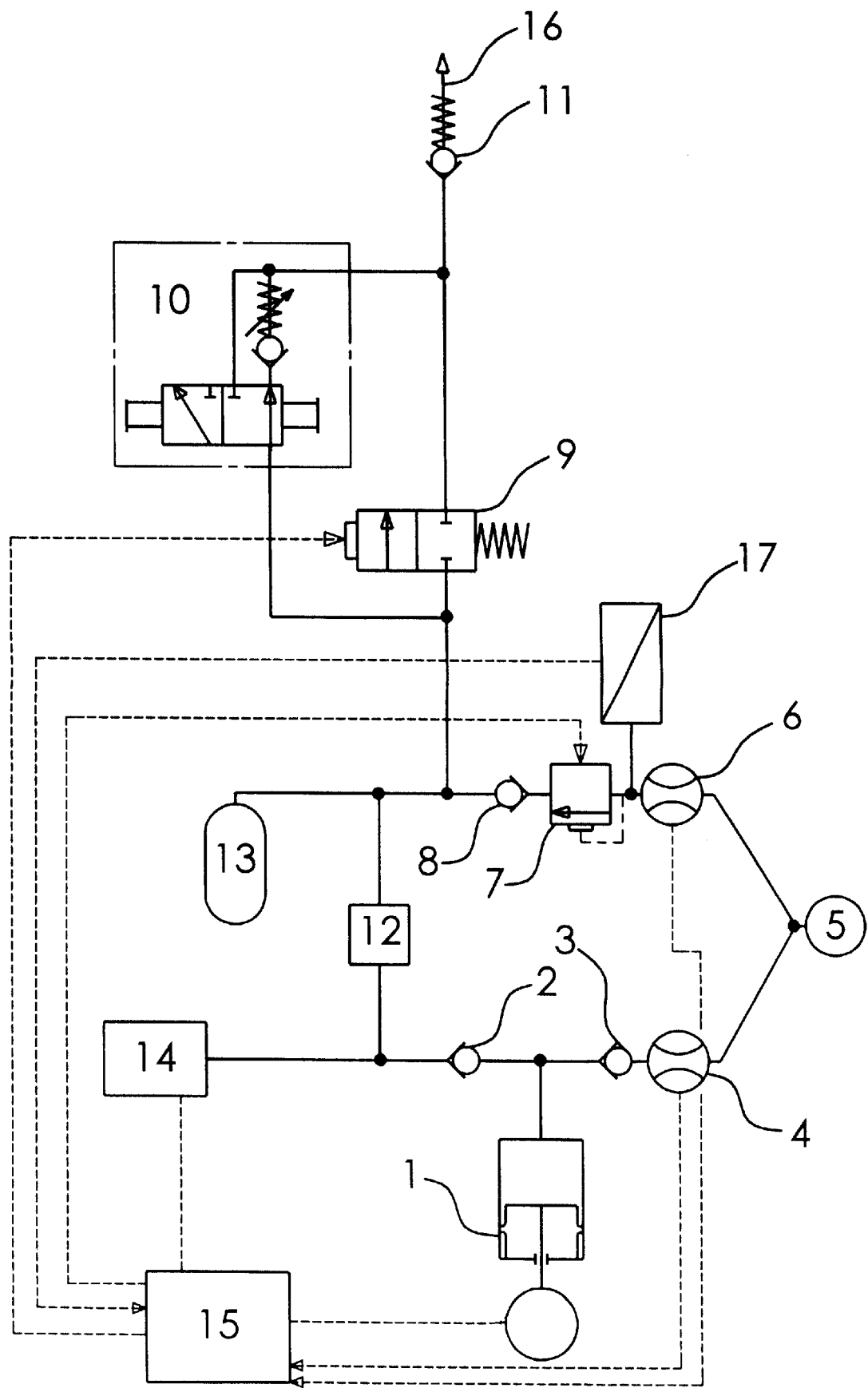

PROCESS FOR CHANGING THE CONCENTRATION IN AN ANESTHESIA APPARATUS

FIELD OF THE INVENTION

The present invention pertains to a process for changing the concentration in an anesthesia apparatus with a breathing circuit with an inspiration branch and an expiration branch, with a fresh gas metering unit and a pressure sensor in the breathing circuit, with a volume displacement means in the inspiration branch and a PEEP/$P_{MAX}$ valve in the expiration branch, wherein the fresh gas metering unit, the pressure sensor, the volume displacement means and the PEEP/$P_{MAX}$ valve are connected to an evaluating and control unit.

BACKGROUND OF THE INVENTION

Anesthesia apparatus which have a volume displacement means as the breathing gas delivery unit for the tidal volume to be applied in the patient have the problem that especially at low respiratory minute volumes, i.e., at low volume displacements per minute, called RMV for short, a change in the anesthetic or fresh gas concentration reaches the patient only very slowly. The cause of this is that the anesthetic or fresh gas fed in newly is not distributed immediately uniformly in the entire breathing circuit of the anesthesia apparatus but gas segments with the new concentration, consisting of anesthetic, fresh gas and a certain percentage of expired gas, move to the patient gradually through the inspiration branch of the breathing circuit with the inspiration stroke. The gas segments with the new concentration are moving toward the patient at a speed proportional to the respiratory minute volume. If very small tidal volumes are to be applied, which occurs, e.g., in the case of neonatal respiration, and also in the case of long tubes, it may take several minutes before the change in concentration in the breathing circuit can be detected at the mouthpiece leading to the patient.

This process cannot be expedited by increasing the fresh gas supply, which will hereinafter also increase fresh gas containing an anesthetic, because anesthesia apparatus with volume displacement means usually operate uncoupled from the fresh gas. If the fresh gas supply is increased, the portion of the fresh gas supply exceeding the respiratory minute volume is discharged unused via the anesthetic gas discharge without a rapid change in concentration taking place at the mouthpiece leading to the patient.

DE 40 04 034 C2 describes an anesthesia respirator with a ventilator as a breathing gas delivery unit, with which a changed set point of an anesthetic gas component can be preset in a time-optimized manner. The control circuit for the system parameters of the breathing circuit is disconnected for a defined period of time, during which the breathing circuit can be flooded with the gaseous anesthetic to be changed. The control circuit is closed again only when a concentration value close to the new set point to be set is reached, as a result of which the controller influences the metering unit of the anesthetic gas in question for setting the new set point.

The drawback of the prior-art anesthesia respirator is that a complicated control circuit is necessary, by means of which a changed anesthetic gas concentration can be brought about in the breathing circuit.

SUMMARY AND OBJECTS OF THE INVENTION

The object of the present invention is to provide a process with which a rapid change in the concentration of the anesthetic or fresh gas being fed can be brought about in the breathing circuit of an anesthesia apparatus without additional design effort.

According to the invention, a process is provided for changing the concentration in an anesthesia apparatus with a breathing circuit. An inspiration branch and an expiration branch are provided with a fresh gas metering unit and a pressure sensor in the breathing circuit, with a volume displacement device in the inspiration branch and a PEEP/$P_{MAX}$ valve in the expiration branch. The fresh gas metering unit, the pressure sensor, the volume displacement device and the PEEP/$P_{MAX}$ valve are connected to an evaluating and control unit. The volume displacement device is completely returned, and the fresh gas supply by the fresh gas metering unit is at the same time increased via the evaluating and control unit such that the volume displacement device is completely filled with the fresh gas fed in. The volume displacement device is moved forward completely, and a set pressure preset on the PEEP/$P_{MAX}$ value is not exceeded in the breathing circuit.

According to another aspect if the invention, a process is provided for changing the concentration in an anesthesia apparatus with a breathing circuit. An inspiration branch and an expiration branch are provided with a fresh gas metering unit and a pressure sensor in the breathing circuit, with a volume displacement device in the inspiration branch and a PEEP/$P_{MAX}$ valve in the expiration branch. The fresh gas metering unit, the pressure sensor, the volume displacement device and the PEEP/$P_{MAX}$ valve are connected to an evaluating and control unit. The fresh gas supply from the fresh gas metering unit is set at the maximum amount that can be metered, and the volume displacement device, controlled by the evaluating and control unit, is returned at the same time at such a speed that the total amount of fresh gas fed by the fresh gas metering unit is taken up by the volume displacement device. The volume displacement device is moved completely forward, and a pressure preset on the PEEP/$P_{MAX}$ valve is not exceeded in the breathing circuit.

One advantage of the process according to the present invention is that a change in concentration reaches the patient very rapidly i.e., within one to three respiration cycles, doing so due to a rinsing operation during the regular operation of the anesthesia apparatus to which the patient is connected.

As an alternative, the rinsing of a volume displacement unit, which displaces the tidal volume to be applied to the patient, can be performed by complete filling with fresh gas either under the control of the fresh gas supply or under the control of the speed, at which speed the volume displacement device is returned for the fresh gas filling. The fresh gas supply and the speed of return are coordinated with one another in both cases such that the volume displacement device is filled completely with fresh gas, and the smallest possible amount of fresh gas is lost unused via the anesthetic gas discharge.

Besides the volume displacement device, the absorber can be rinsed as well. Depending on whether and how the volume displacement device is located in the inspiration branch of the breathing circuit or in another area of the breathing circuit, it must be subsequently rinsed after the rinsing of the volume displacement device, or it can be rinsed already simultaneously in the second case, as a result of which the entire process is shortened in time.

Moreover, the process according to the present invention can be used in a versatile manner, namely, for both pressure-controlled respiration and volume-controlled respiration, and only an additional process step is to be performed first in the latter case, namely, the end inspiratory pressure is measured in the breathing circuit and the measured value is stored in order to preset in the last step a maximum pressure below which the volume displacement device is moved forward. The possibility of use covers volume displacement device which displace the volume in their front range of displacement and in their rear range of displacement alike.

Further details of the present invention will be explained on the basis of the exemplary embodiment shown in the drawing.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

BRIEF DESCRIPTION OF THE DRAWING

In the drawing:

The only FIGURE is a schematic view of an anesthesia apparatus which can be operated with the process according to the present invention.

DESCRIPTION OF THE PREFERRED EMBODIMENT

Referring to the drawings in particular, a volume displacement device 1 displaces the tidal volume to be applied into a breathing circuit with a first nonreturn valve 2 for uncoupling the fresh gas and with second and third nonreturn valves 3 and 8 for presetting the direction in the breathing circuit. The tidal volume displaced to a patient 5 is measured with a first volume flow sensor 4, and the volume of breathing gas expired by the patient 5 is measured with a second volume flow sensor 6. To seal off the breathing circuit from the outside during the phase of inspiration and to achieve the build-up of the breathing gas pressure which is necessary for the application of the tidal volume, a PEEP/$P_{MAX}$ valve 7 (PEEP is the abbreviation of Positive End Expiratory Pressure) is used, which has a pressure setting at the level of the preset pressure $P_{MAX}$ for inspiration and a pressure setting at the level of PEEP for expiration and is closed as long as the pressure of the breathing gas in the breathing circuit is below the pressure setting. $P_{MAX}$ is a safety pressure set by the user, which is not reached during normal operation. The airway pressure is measured with a pressure sensor 17. The carbon dioxide present in the volume of breathing gas expired by the patient 5 is removed from the breathing circuit by an absorber 12, and fresh gas is fed in via the fresh gas metering unit 14. The fresh gas metering unit 14, the volume displacement device 1, the pressure sensor 17, the PEEP/$P_{MAX}$ valve 7, the volume flow sensors 4 and 6, and a reversing valve 9 are connected to an evaluating and control unit 15. The reversing valve 9 is used for changeover between automatic respiration, on the one hand, and manual respiration or spontaneous breathing, on the other hand. In the case of manual respiration, the necessary breathing gas pressure in the breathing circuit is generated by device of a manual respiration bag 13 and is limited upward by a pressure-limiting valve 10. The pressure-limiting valve 10 has an integrated switch, with which a bypass line for the spontaneous breathing can be closed. A fourth nonreturn valve 11 prevents expired breathing gas from being rebreathed by the patient 5 from an anesthetic gas discharge 16 in case of lack of fresh gas supply during respiration via the manual respiration bag 13 or during spontaneous breathing and the resulting vacuum in the breathing circuit. The suitable volume displacement device 1 may be, e.g., a reciprocating pump, a bellows, a bag or a diaphragm chamber.

The process according to the present invention is explained in connection with a volume-controlled respiration cycle. The application to pressure-controlled respiration is analogous, with the only difference that a maximum respiration pressure is automatically preset in the case of pressure-controlled respiration, whereas it must be set in a separate first step in the case of volume-controlled respiration.

In a first step, the end expiratory pressure, also called plateau pressure, is measured by the pressure sensor 17, and this pressure is stored in the evaluating and control unit 15 as the above-mentioned maximum respiration pressure.

The piston of the volume displacement device 1 is then returned completely during the phase of expiration from its normal respiration position, which meters the tidal volume to be applied at the upper end of the range of displacement of the volume displacement device 1. At the same time, the fresh gas supply is increased by the fresh gas metering unit 14 via the evaluating and control unit 15 such that complete filling of the volume displacement device 1 with the fresh gas being fed by the fresh gas metering unit 14 is guaranteed. This second step is the complete fresh gas filling of the volume displacement device 1 under the control of the fresh gas supply.

As an alternative to this, the complete fresh gas filling of the volume displacement device 1 takes place under the control of the speed at which the piston is returned. The fresh gas supply is now set by the fresh gas metering unit 14 at the maximum amount that can be metered and the piston of the volume displacement device 1, controlled by the evaluating and control unit 15, is returned at the same time at the speed arising from the fresh gas supply. With this device the piston returns so rapidly that all the fresh gas fed in by the fresh gas metering unit 14 is taken up by the volume displacement device 1 without fresh gas escaping unused via the anesthetic gas discharge 16.

In a third step, with the beginning of the phase of inspiration, the PEEP/$P_{MAX}$ valve 7 is set by the evaluating and control unit 15 at the maximum respiration pressure (plateau pressure) that is measured in the first step by the pressure sensor 17 and is stored by the evaluating and control unit 15, and the piston of the volume displacement device 1 is moved forward from its lower end position, in which the volume displacement device 1 is completely filled with fresh gas, into the upper end position, in which the total amount of fresh gas was pushed out of the volume displacement device 1. The volume of fresh gas being displaced to the patient 5 now exactly corresponds to the tidal volume to be applied. The airway pressure in the breathing circuit is now limited upward by the plateau pressure set on the PEEP/$P_{MAX}$ valve 7. The excess fresh gas volume is pressed via the PEEP/$P_{MAX}$ valve 7 into the anesthetic gas discharge 16 and is discharged from there.

At the same time, the fresh gas supply from the fresh gas metering unit 14, controlled by the evaluating and control unit 15, is guaranteed in the third step for rinsing the absorber 12, which can take up a gas volume of approximately 1.5 L. The time period for the third step may have to be extended in order to completely rinse the absorber 12 with the fresh gas fed in.

If this process, which comprises the three steps explained, is applied to a volume displacement device 1 in which the fresh gas volume is displaced in the rear range of displacement of the volume displacement device 1 rather than in the front range of displacement, the volume displacement device 1 must be completely emptied according to the procedure described in the third step before it is filled up.

The duration of the process according to the present invention is one and a half respiration cycles rather than one respiration cycle in this case. Furthermore, the above-described process must be carried out twice consecutively in the case of an anesthesia apparatus with a breathing circuit in which both the volume displacement device 1 and the absorber 12 are located in the inspiration branch: It must be performed once to rinse the volume displacement device 1 and once to rinse the absorber 12, because, contrary to the above-described third step of the process, the absorber 12 cannot be rinsed simultaneously in time for emptying the volume displacement device 1 if it is also located in the inspiration branch.

The process according to the present invention makes it possible to rinse the breathing circuit, comprising the volume displacement device 1, the absorber 12 and the tubes of the breathing circuit within one or two breathing cycles, which may be prolonged, so that a change in the concentration of the components of the fresh gas reaches the patient 5 very rapidly via the tidal volume to be applied.

In addition, the amount of fresh gas that is needed for rinsing the breathing circuit in the process according to the present invention is minimal.

The process according to the present invention will be illustrated by the following numerical example:

During the operation of an anesthesia apparatus with a (comparatively low) respiratory minute volume of 3.75 L per minute and a fresh gas supply at the level of 4 L per minute from the fresh gas metering unit 14, it takes about 250 sec for a change in the oxygen concentration from 21% to 100% in the fresh gas to reach the patient 5. If the process according to the present invention is used, and the fresh gas metering unit 14 is set at the maximum amount that can be metered, which is 18 L per minute, in the second step, and the speed at which the piston of the volume displacement device 1 is returned is controlled correspondingly, 4.7 sec are needed for the fresh gas filling of the volume displacement device 1 in the second step and approx. 3 sec are needed for "pushing out" the volume displacement device 1 in the subsequent, third step, i.e., about 8 sec are needed for carrying out the entire process. Even if it is assumed that one respiration cycle is not sufficient for completely rinsing the breathing circuit and rinsing is carried out in three respiration cycles for safety's sake, the desired change in concentration is achieved in about 24 sec, i.e., less than one tenth of the time of 250 sec needed according to the prior art.

While specific embodiments of the invention have been shown and described in detail to illustrate the application of the principles of the invention, it will be understood that the invention may be embodied otherwise without departing from such principles.

What is claimed is:

1. A process for changing the concentration in an anesthesia apparatus with a breathing circuit, the process comprising the steps of:

providing a breathing circuit with an inspiration branch and an expiration branch, with a fresh gas metering unit connected to the breathing circuit and a pressure sensor in the breathing circuit, with a volume displacement device in the inspiration branch and a Positive End Expiratory Pressure (PEEP)/maximum pressure ($P_{MAX}$) valve in the expiration branch;

connecting an evaluating and control unit to the fresh gas metering unit, the pressure sensor, the volume displacement device and the PEEP/$P_{MAX}$ valve;

completely returning the volume displacement device to a start position and substantially at the same time increasing the fresh gas supply from the fresh gas metering unit via the evaluating and control unit such that the volume displacement device is completely filled with the fresh gas fed in; and moving the volume displacement device forward completely while not exceeding a set pressure preset on the PEEP/$P_{MAX}$ valve in the breathing circuit.

2. A process in accordance with claim 1, wherein the pressure preset on the PEEP/$P_{MAX}$ valve is the end inspiratory pressure measured previously by a pressure sensor and stored by the evaluating and control unit.

3. A process in accordance with claim 1, wherein an absorber is located in the breathing circuit but not in the inspiration branch, the absorber being rinsed at the same time with fresh gas from the fresh gas metering unit in the step of moving the volume displacement device forward completely while not exceeding a set pressure preset on the PEEP/$P_{MAX}$ valve in the breathing circuit.

4. A process in accordance with claim 1, wherein an absorber is located in the inspiration branch and is rinsed with fresh gas from the fresh gas metering unit in an additional step following said step of moving the volume displacement device forward completely while not exceeding a set pressure preset on the PEEP/$P_{MAX}$ valve in the breathing circuit.

5. A process in accordance with claim 1, wherein the volume displacement device is moved completely forward in an additional step such that the volume displacement device is emptied to the breathing circuit, which is carried out before said step of completely returning the volume displacement device to a start position and substantially at the same time increasing the fresh gas supply from the fresh gas metering unit.

6. A process in accordance with claim 1, wherein a reciprocating piston pump, a bellows, a bag or a diaphragm chamber is used as the volume displacement device.

7. A process for changing the concentration in an anesthesia apparatus with a breathing circuit, the process comprising the steps of:

providing the breathing circuit with an inspiration branch and an expiration branch, with a fresh gas metering unit connected to the breathing circuit and a pressure sensor in the breathing circuit, with a volume displacement device having an expansible chamber connected in fluid communication with the inspiration branch for receiving gas from the inspiration branch and displacing gas to the inspiration branch and a Positive End Expiratory Pressure (PEEP)/maximum pressure ($P_{MAX}$) valve in the expiration branch;

connecting an evaluating and control unit to the fresh gas metering unit, the pressure sensor, the volume displacement device and the PEEP/$P_{MAX}$ valve;

setting the fresh gas supply from the fresh gas metering unit at the maximum amount that can be metered, and controlling the volume displacement device with the evaluating and control unit to receive gas from the inspiration line at the same time at a speed that an amount of fresh gas fed by the fresh gas metering unit is taken up by the volume displacement device; and moving the volume displacement device completely forward while not exceeding a pressure preset on the PEEP/$P_{MAX}$ valve in the breathing circuit.

8. A process in accordance with claim 7, wherein the pressure preset on the PEEP/$P_{MAX}$ valve is the end inspiratory pressure measured previously by a pressure sensor and stored by the evaluating and control unit.

9. A process in accordance with claim 7, wherein an absorber is located in the breathing circuit but not in the inspiration branch, the absorber being rinsed at the same time with fresh gas from the fresh gas metering unit in the step of moving the volume displacement device forward completely while not exceeding a set pressure preset on the PEEP/$P_{MAX}$ valve in the breathing circuit.

10. A process in accordance with claim 7, wherein an absorber is located in the inspiration branch and is rinsed with fresh gas from the fresh gas metering unit in an additional step following said step of moving the volume displacement device forward completely while not exceeding a set pressure preset on the PEEP/$P_{MAX}$ valve in the breathing circuit.

11. A process in accordance with claim 7, wherein the volume displacement device is moved completely forward such that the volume displacement device is emptied to the breathing circuit in an additional step, which is to be carried out before said step of setting the fresh gas supply from the fresh gas metering unit at the maximum amount that can be metered, and controlling the volume displacement device with the evaluating and control unit to return at the same time at a speed that the total amount of fresh gas fed by the fresh gas metering unit is taken up by the volume displacement device.

12. A process in accordance with claim 7, wherein a reciprocating pump, a bellows, a bag or a diaphragm chamber is used as the volume displacement device.

13. An anesthesia apparatus, comprising:
a breathing circuit with an inspiration branch and an expiration branch;
a fresh gas metering unit connected to said breathing circuit;
a pressure sensor in the breathing circuit;
a volume displacement device having an expansible chamber connected in fluid communication with the inspiration branch for receiving gas from the inspiration branch and displacing gas to the inspiration branch;
a positive end expiratory pressure (PEEP)/maximum pressure ($P_{MAX}$) valve in the expiration branch;
an evaluating and control unit connected to said gas metering unit, connected to said pressure sensor, connected to said volume displacement device and connected to said PEEP/$P_{MAX}$ valve, said evaluating and control unit controlling said volume displacement device and said gas supply to:
completely return the volume displacement device to a start position while increasing the gas supply from the gas metering unit via the evaluating and control unit such that the volume displacement device is completely filled with the gas fed in or set the gas supply from the gas metering unit at the maximum amount that can be metered, and control the volume displacement device to receive gas from the inspiration branch at a rate that the gas fed by the gas metering unit is taken up by the volume displacement device; and
move the volume displacement device to displace the gas completely while not exceeding a set pressure preset on the PEEP/$P_{MAX}$ valve in the breathing circuit.

* * * * *